United States Patent [19]
Deutchman et al.

[11] Patent Number: 5,395,379
[45] Date of Patent: Mar. 7, 1995

[54] EXTRACTOR FOR CHILDBIRTH AND ASPIRATOR/INJECTOR DEVICE

[76] Inventors: Mark E. Deutchman, 1609 Oak Hill Rd., Memphis, Tenn. 38138; Arnold H. Deutchman, 2200 Lane Rd., Columbus, Ohio 43220

[21] Appl. No.: 94,703
[22] Filed: Jul. 22, 1993
[51] Int. Cl.$^6$ .............................................. A61B 17/42
[52] U.S. Cl. ..................................... 606/123; 604/227
[58] Field of Search ............................ 294/64.1–64.3, 294/65; 604/35, 37, 38, 73–75, 140–149, 181, 187, 213, 218, 221, 222, 227, 228, 902, 313, 314–316; 606/1, 119, 121, 122, 123

[56] References Cited

U.S. PATENT DOCUMENTS

| | | |
|---|---|---|
| 160,037 | 2/1875 | Stillman . |
| 2,379,629 | 7/1945 | Eweson ............................ 294/64.1 |
| 3,202,152 | 8/1965 | Wood et al. . |
| 3,592,198 | 7/1971 | Evans . |
| 3,765,408 | 10/1973 | Kawai . |
| 3,794,044 | 2/1974 | Vennard et al. . |
| 3,819,091 | 6/1974 | Hollender . |
| 3,957,051 | 5/1976 | Topham . |
| 3,957,052 | 5/1976 | Topham . |
| 4,730,617 | 3/1988 | King . |
| 4,925,449 | 5/1990 | Saez et al. ............................ 604/218 |
| 4,997,420 | 3/1991 | LeFevre . |
| 5,011,381 | 4/1991 | Neward . |
| 5,019,086 | 5/1991 | Neward . |
| 5,241,969 | 9/1993 | Carson et al. ...................... 604/227 |

*Primary Examiner*—Stephen C. Pellegrino
*Assistant Examiner*—Glenn K. Dawson
*Attorney, Agent, or Firm*—Sidney W. Millard

[57] ABSTRACT

A medical device which is manually operable to draw a vacuum using a piston and cylinder combination may be used for creating a vacuum in the cup of a birth extraction device or to withdraw fluids from a body cavity or perform biopsies. The structure includes a closed loop at the remote end of the cylinder which allows the device to be manipulated by one hand and it may include check valves to prevent any fluid withdrawn from the body from being reinjected into the body cavity or vessel by location of check valves in a withdrawal duct and a drainage port. The same device may be used for injecting fluids into a body cavity and may include structure between the loop and cylinder to apply force to the piston to discharge fluids through a needle attached to the remote end of the cylinder.

28 Claims, 4 Drawing Sheets

EXTRACTOR FOR CHILDBIRTH AND ASPIRATOR/INJECTOR DEVICE

FIELD OF THE INVENTION

This invention relates to a piston and cylinder combination used to create a vacuum on a birth cup to assist in the delivery of an infant. A similar piston and cylinder structure may be used to withdraw fluids from body cavities, perform needle biopsies of soft tissues and solid organs, inject substances into the body, or transfer fluids from one vessel to another or otherwise create low volume, high pressure vacuum for medical or industrial uses.

BACKGROUND OF THE INVENTION

The original concept of this invention arose from difficulties encountered by one of the inventors in hospital delivery rooms where the structure and associated apparatus of existing obstetric vacuum extractors for assisting childbirth proved to be cumbersome.

Modern technology has advanced considerably in providing apparatus to monitor the progress of mothers in labor and the condition of the fetus during labor. The process of vaginal birth may be assisted by hard steel forceps or a variety of available vacuum extraction devices. Although forceps are highly effective when used in the proper circumstances, vacuum extraction devices are less likely to cause maternal or infant injury and can replace forceps in many cases.

Existing vacuum extractor devices include a variety of obstetric vacuum cups on the end of a handle combined with a hose attached to an external vacuum source. The procedure for using the vacuum extractor is to draw a vacuum on the cup only during uterine contractions. The vacuum cup is intended to hold on to the baby's head and to assist the birth by allowing the physician to pull on the baby's head as the mother pushes. Upon the cessation of each contraction, the vacuum is released until the next contraction begins. The reasons for this procedure are well known in the field and need not be discussed here.

The main problem with existing apparatus is the need for control of an external vacuum source. This requires either the physician's free hand or a second person with coordinated action between the physician and this second person. Additionally, the speed of response in drawing the vacuum is directly proportional to the volume and diameter of the hoses and ducts intermediate the vacuum cup and the vacuum pump. The greater the length of the tubes and the larger the diameter involved, the longer it will take to evacuate the system and produce the vacuum needed to secure the cup to the baby's head.

It must be possible to repeatedly and quickly regenerate the vacuum for these reasons:

1) Air leakage between the cup and the baby's head is common, reducing the hold of the cup on the baby's head. This leakage is due to the baby's hair, wires used for electronic fetal heartbeat monitoring, and partial cup disengagement.
2) Fluids such as amniotic fluid, blood and vernix commonly enter the cup and occupy some space.
3) The vacuum is purposely interrupted between uterine contractions and must be regenerated to enable the physician to pull and assist the birth.

SUMMARY OF THE INVENTION

The inventive concept which will be described subsequently resulted in a vacuum pump combined with a vacuum cup where the physician is in complete control by hand manipulation of the degree of vacuum drawn on the cup at all times and the whole process may be controlled and manipulated by one hand while the physician's other hand performs any other needed services during the process.

The uniqueness of this device is that its operation in all its embodiments is performed through the natural squeezing motion of the hand. The squeezing motion of the human hand is its strongest and most natural action.

A valve system, either integral or detachable, can serve to maintain or release the vacuum. The same valve system allows exhaust of leaked fluids or air and regeneration of the vacuum.

As a result of the invention made specifically in relation to obstetrics, the structural features showed promise for use as a vacuum syringe for withdrawing bodily fluids or performing biopsies of soft tissues or solid organs by substituting a needle for the obstetric vacuum cup. A further concept allows a physician to use the same needle and vacuum apparatus to inject substances into a body using essentially the same structure using a one-handed squeezing motion to draw up the substance to be injected and with a return spring in the cylinder-piston combination to effect the injection stroke as an autoinjector. Alternatively, finger and thumb holes allow the physician to effect or assist the injection stroke. An additional further concept is to use both the vacuum and injection features alternatively to create a pumping action to fill or evacuate body cavities or other vessels.

As to the obstetric vacuum cup invention, any particular cup currently available may be adapted to the use with the general apparatus of this invention which includes a piston and cylinder combination uniquely structured to serve the desired purpose of the inventors. It includes a frame, an axially aligned piston and cylinder combination secured in the frame, and a closed loop secured to one side of the frame and extending therefrom to circumscribe a handle on the remote end of the piston and looping around to be attached to the other side of the frame. The handle is configured such that the palm of the physician's hand may be located at the outer portion of the loop while the fingers of the same hand grip the transversely extending handle and draw it toward the palm by squeezing thereby creating a vacuum in the cylinder. This creates the necessary vacuum on the obstetric cup in the conventional fashion. A check valve in line with the cylinder and cup acts to maintain the vacuum in the cup upon release of the handle. A vacuum gauge with appropriate indicia can be formed in the frame to allow the physician to observe the degree of vacuum applied during the process if required. Thereby, when the desired degree of vacuum is achieved, the physician may release the piston handle and apply the pulling action to the loop rather than continue to pull on the handle and draw too great a vacuum or if maximum vacuum is required, the physician may pull the handle and loop together, grasped within the hand.

A spring bias working between the loop and the outermost end of the piston serves to drive the piston toward the innermost end of the cylinder in a return stroke. This return stroke serves to discharge liquids or air from the cylinder which have been withdrawn during the vacuum application stroke. Such fluids are discharged through a side duct. An exhaust valve mounted in the side duct opens during the return stroke to allow the expulsion of any air or fluids that have entered the cylinder, thereby preparing for another squeeze of the operator's hand to restore or increase the vacuum. Alternatively, finger holes in the frame adjacent to the cylinder permit a squeezing motion of the hand to apply a linear force to depress the piston to aid in exhausting leaked liquids or air from the cylinder. The size and structure of the exhaust port and various valves prevent them from being clogged by hair, vernix, blood or amniotic fluid, yet not leak air. The vacuum range of the device is up to about 600 mm HG or 11.6 lb/in$^2$.

A quick release of the vacuum in the cup upon the ending of a contraction is accomplished by opening a release valve. The release is spring biased to close a short passage in the frame, which passage leads directly to the passage between the cup connection and the forwardmost end of the cylinder. The release valve is so located that the thumb of the physician may open it to allow air to rush into the vacuum through the short passage and relieve the vacuum almost instantaneously. Note that this is still an one-handed instrument because of the location of the valve.

This same general structure may be used for extracting body fluids from a cavity, providing a needle biopsy of soft tissue or solid organs or providing the controlled injection of fluids into a body cavity or blood vessels. Medical procedures commonly applicable include:
Thoracentesis
Arthrocentesis
Paracentesis
Peritoneal lavage
Wound or eye irrigation
Percutaneous liver biopsy
Percutaneous kidney biopsy
Aspiration or biopsy of masses or tumors such as breast masses
Bone marrow aspiration
Chorionic villus sampling
Amniocentesis
Radiographically or sohographically-guided biopsies or aspiration
Drawing up into a syringe and subsequent injection of dyes or contrast agents for a variety of applications including angiograms, intravenous pyelography, choangiography, hysterosalpingography, fine needle aspiration and biopsy when fitted with a wider diameter flange, used to apply vacuum to skin for dermatologic applications such as cyst evacuation or comedone extraction.

While the invention is described generally in relation to living animals and not limited to humans, it will be clear that the device will be applicable to evacuating gas or fluids from a cavity or vessel or transferring gas or fluids from one cavity to another regardless of whether the cavities exist in a living organism.

If hoses are connected to the intake and exhaust ports, the device may be used to transfer fluids from one vessel to another or simply to create a low volume, high pressure vacuum for other medical, laboratory or industrial applications.

Objects of the invention not understood from the above, will be fully appreciated upon a review of the drawings and a reading of the Description of the Preferred Embodiments which follows.

DESCRIPTION OF THE PREFERRED EMBODIMENTS

Figure 1:
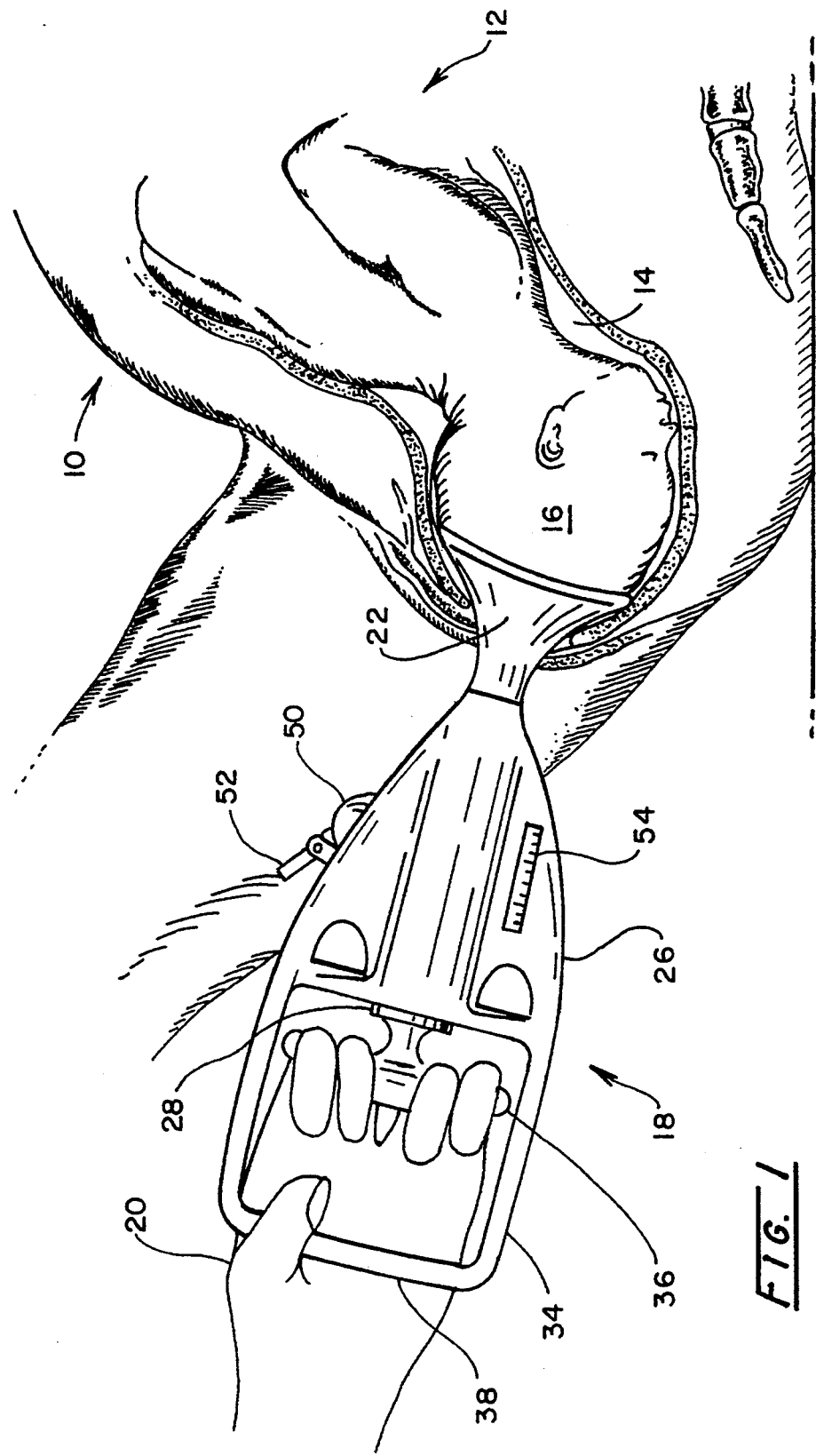
FIG. 1 is a perspective, isometric, elevational view of the reproductive portion of a human female showing a fetus in a normal birth position and with the apparatus of the present invention secured to the head of the fetus.

Referring now to FIG. 1, there is depicted a human female designated generally at 10 in the position commonly assumed during child birth. The fetus or infant designated generally at 12 is positioned in the birth canal 14 with its head 16 in the normally downwardly directed position. The obstetrical delivery apparatus of the present invention designated generally at 18 is gripped by the hand 20 of a physician.

Figure 2:
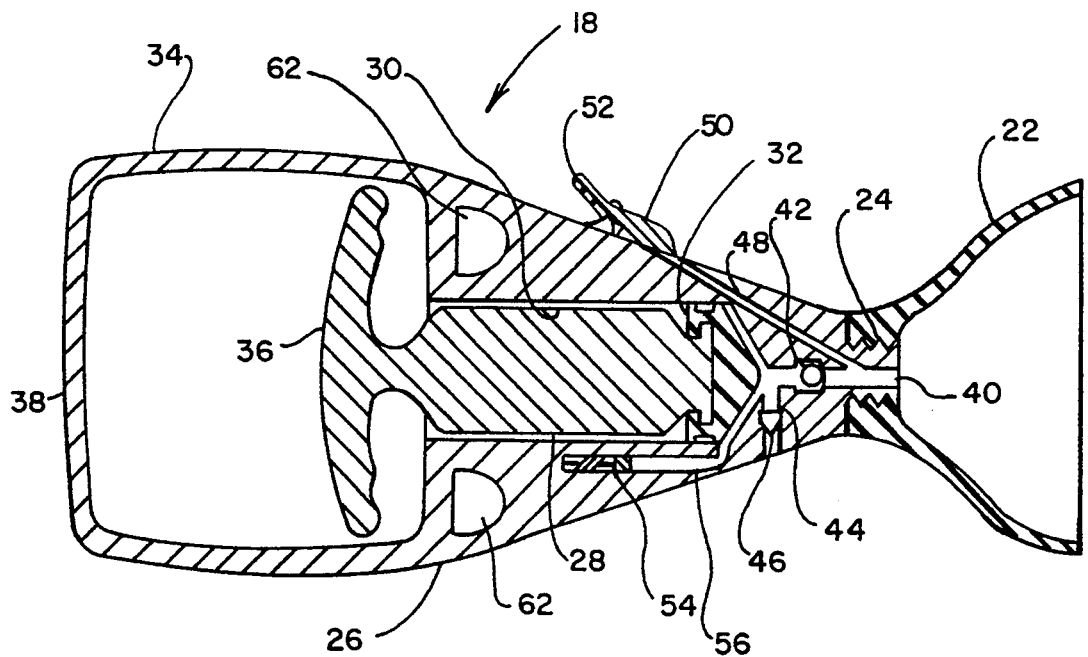
FIG. 2 is a sectional view of a first embodiment of the extractor of FIG. 1.
Figure 3:
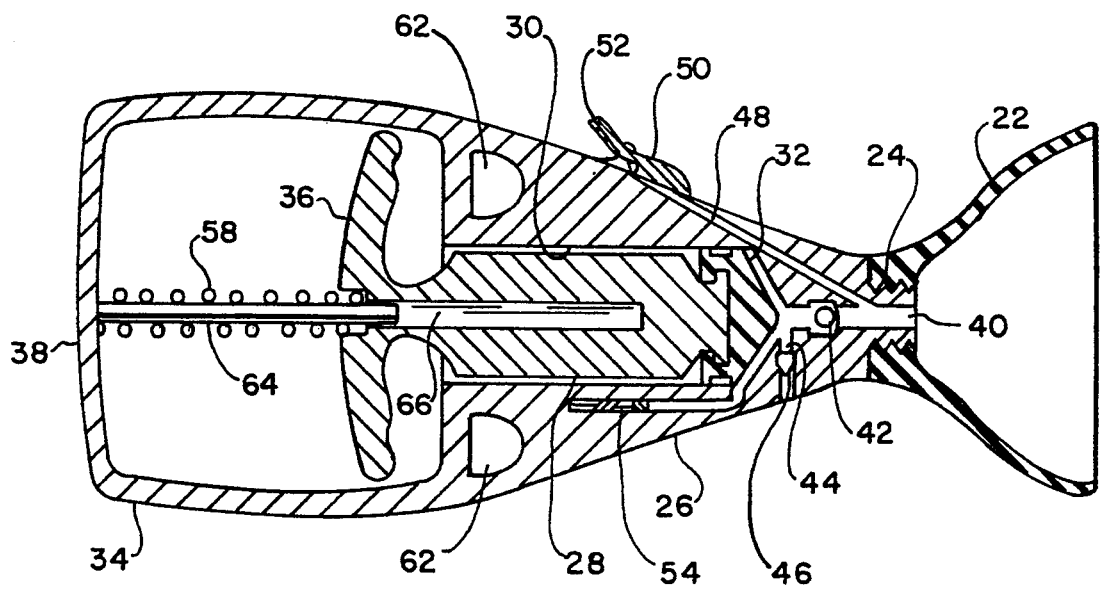
FIG. 3 is a sectional view of a second embodiment of the extractor.

Looking further at FIGS. 1-3, the delivery apparatus 18 includes a cup 22 for fitting over the head 16 of the fetus, to grip the same and assist the physician in the birth process. The cup 22 is connected at 24 by threads or other convenient means to one end of a frame 26. A piston 28 and cylinder 30 combination are mounted in rigid operable position in the frame whereby the piston 28 may reciprocate coaxially with the cylinder 30 as will explained in more detail subsequently.

A conventional seal element 32 is mounted on the forward end of the piston 28 to provide a fluid tight seal between the piston and the sidewalls of the cylinder 30 to allow a vacuum to be drawn on the cup 22 upon the retraction of the piston from the forward end of the cylinder.

The frame 26 includes a loop 34 projecting from one side of the frame to circumscribe a transversely extending handle 36 on piston 28. The purpose of the handle 36 is to allow the fingers of the physician's hand 20 to encircle the handle while the thumb rests on the remote portion 38 of loop 34 as seen in FIG. 1.

A first passageway 40 extends from the inside of cup 22 through the forward portion of the framework 26 into fluid communication with the forward end of cylinder 30 to allow liquids or gases to be drawn from cup 22 as it embraces the head of the fetus to draw a vacuum thereon and maintain a secure connection allowing the physician to pull the head of the fetus partially through the birth canal upon the uterine contraction of the mother during the birthing process. A first check valve 42 is configured to allow the passage of fluid through passage 40 from cup 22 into the cylinder upon the retraction of the piston 28. However, valve 42 is oriented to prevent the reinjection of withdrawn fluids into the cup 22 upon the forward advance of the piston after the vacuum is released in cup 22 at the cessation of the contraction of the mother.

In order to expel the liquids and gases withdrawn through passage 40 into cylinder 30 a second or exhaust passage or opening 44 is provided. Passageway 44 opens into passageway 40 and as the piston 28 reciprocates toward the forward end of cylinder 30, check valve 42 closes and the fluids are forced to flow through second passage 44 which allows the discharge of such fluids through a second check valve 46.

A third passageway 48 is formed in the frame to extend to the first passageway 40 intermediate the cup 22 and the check valve 42. Its outermost opening at a remote area of the frame is closed by a sealing valve 50 having a thumb lever 52 which allows the physician to use his thumb to depress lever 52 and thereby lift valve 50 and open third passageway 48 to the atmosphere. Opening valve 50 allows air from the atmosphere to flow through passages 48 and 40 into cup 22 and thereby relieve the vacuum created by the retraction of piston 28 in cylinder 30.

During the birthing process where the physician wishes to assist the fetus through the birth canal and the vacuum is drawn on cup 22, it is important that the optimum vacuum be drawn to minimize injuries to the fetus and maximize the ability of the doctor to give assistance at the right time. To achieve this desired result, a vacuum gauge 54 is provided in the frame 26 in fluid communication with a fourth passageway 56 which is in fluid communication with passage 40 and the forward end of cylinder 30.

In operation the physician folds the cup 22 which is very flexible to insert it into the birth canal as illustrated in FIG. 1 and into engagement with the head 16 of the fetus 12. Upon a uterine contraction the physician may, using only one hand, draw a vacuum in cup 22 to secure the head 16 to the framework 26 by using any of the embodiments illustrated in FIGS. 2-5. This is accomplished by the fingers of the physician gripping the underside of handle 36 while his thumb hooks over the remote handle portion 38 of loop 34 and he squeezes to retract the piston 28 from the forward end of the cylinder 30. Thereby gases and liquids are evacuated from the cup 22. Such fluids flow through passage 40 and check valve 42 into cylinder 30. The squeezing continues until the desired vacuum is observed by the physician at the vacuum gauge 54.

At that point in time the squeezing can cease and the handle 36 may be released by the physician because the vacuum will remain. The physician may then pull to assist birth using the loop 34 for the pulling operation.

Figure 4:
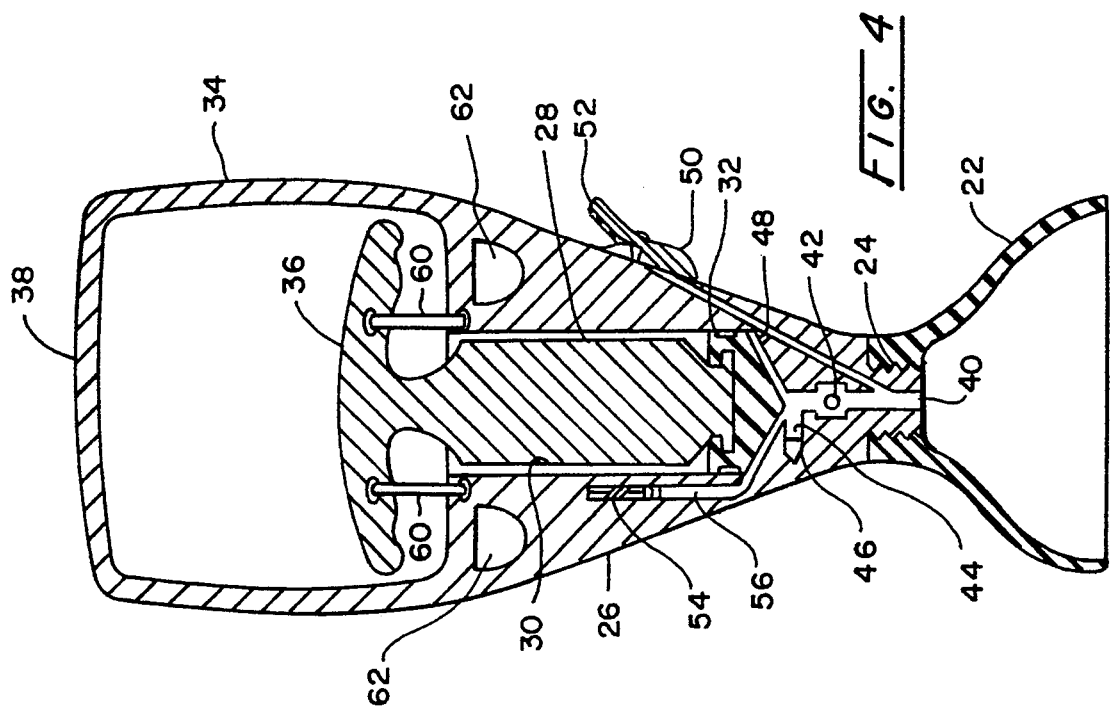
FIG. 4 is a sectional view of a third embodiment of the extractor.

Upon a release of the handle 36 by the physician's hand 20, the existing vacuum in cylinder 30 is relieved and the piston moves toward the forward end of the cylinder by itself or by (1) a spring bias 58 shown in FIG. 3, (2) a pair of elastomeric bands 60 as illustrated in FIG. 4 or (3) the piston may be depressed by the hand of the physician using finger holes 62 and manually depressing the handle 36 by the thumb of the hand. Whatever mechanism moves the piston 28 to the forward end of cylinder 30, the fluids drawn into cylinder 30 are expelled through opening 44 because the check valve 42 seals the first passageway 40 immediately upon the pressure in the cylinder exceeding the pressure in cup 22 and second check valve 46 opens.

The check valve 46 allows the entrained fluids in cylinder 30 to exit the frame 26 away from the birth canal and not be reinjected into it through passageway 40 and cup 22.

The point in time when the uterine contractions of the mother begin is the time the physician wants to draw the vacuum as quickly as possible to help the birth by pulling. That is something which the physician can obtain almost instantly in this invention by a squeezing of the handle 36 and the remote portion 38 of the loop. The desired degree of vacuum can be maintained during the contraction and the physician can pull as indicated previously until the contraction recedes. At that point in time it is important to relieve the vacuum on cup 22 and this is accomplished by the thumb of the physician depressing valve lever 52 and lifting sealing valve 50 to allow atmospheric air to rush into the cup 22 through passages 48 and 40. Thus, the vacuum in the cup is relieved for the period of time when the uterine contraction is not taking place. As indicated previously, the reasons for this rhythmic procedure is known in the art and it is not necessary to describe the same.

Figure 5:
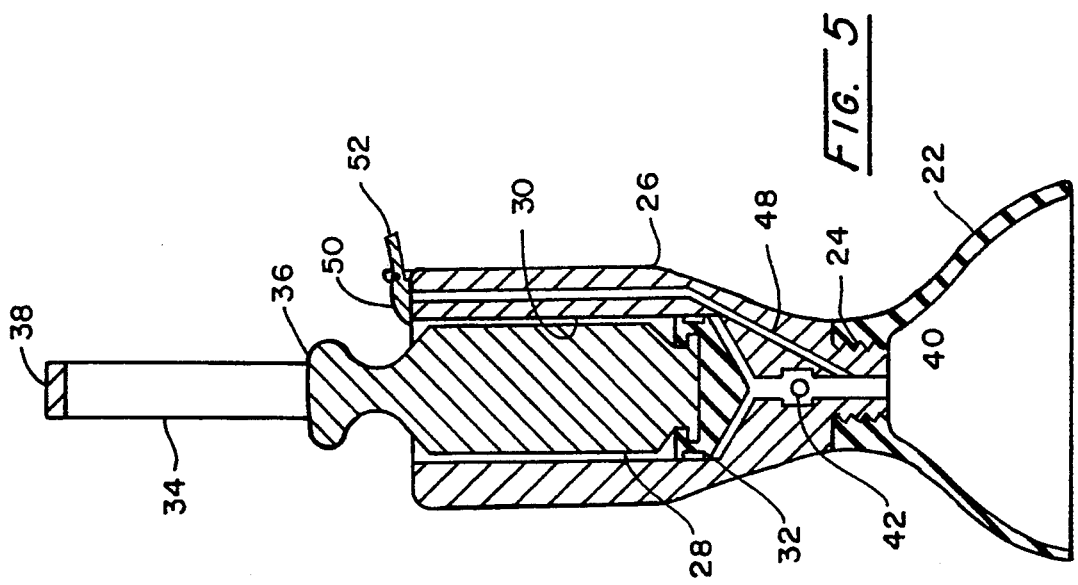
FIG. 5 is a sectional view of a fourth embodiment of the extractor.

Note the locations of the sealing valve 50 in FIGS. 2-4 and the alternate location shown in FIG. 5. The particular location on the frame is not material to the operation of the apparatus so long as it is easily and quickly accessible to the thumb of the physician.

FIG. 3 indicates a particular mechanism for maintaining axial alignment between the piston and cylinder by providing a guide means 64 in the form of a rod extending coaxially with the piston through the handle and into a bore 66 which is also coaxially aligned with the piston and cylinder combination.

Figure 6:
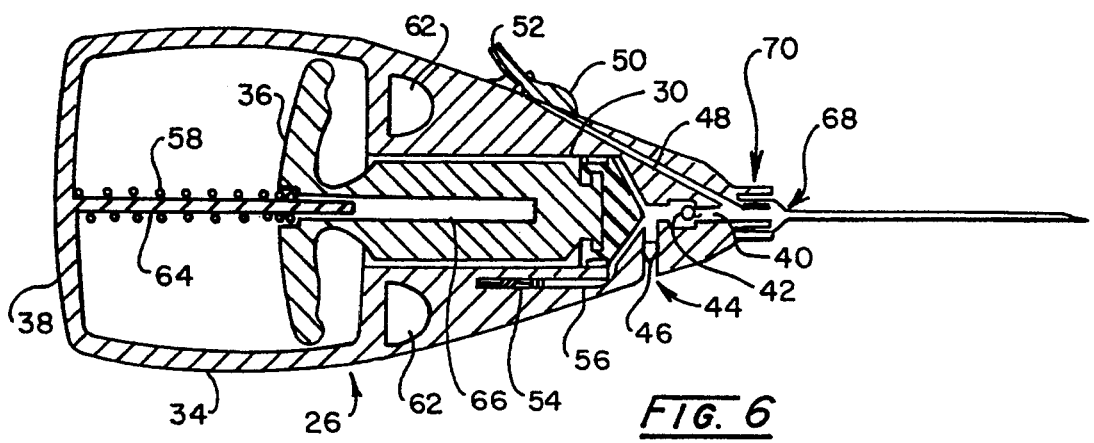
FIG. 6 is a sectional view of a fifth embodiment of the invention where the apparatus includes a hollow needle at one end.

FIG. 6 is a modification of the embodiments illustrated in FIGS. 1-5 in that a hollow needle 68 is secured to the forward end of the frame 26 by a standard luer lock 70 in the conventional fashion. This particular embodiment could be used as a pump to withdraw a rather substantial amount of fluid or other material from a body cavity penetrated by needle 68 in that the piston could be withdrawn and depressed a plurality of times to obtain the desired amount of material. Emptying of fluid from the cylinder 30 can be accomplished manually by using finger holes 62 and squeezing or automatically by biasing means 58 and 64. Any commonly available tubing can be attached to exhaust port 44 where it opens into frame 26 for the purpose of collecting the fluid being pumped out or to maintain a closed, sterile system if needed. With commonly available adapters, the needle attached at 70 and collection tubing attached at 44 can be reversed permitting the device to be used to pump fluids either in or out of a body cavity or other container. Medical applications include paracentesis, thoracentesis, peritoneal lavage or dialysis, etc. Laboratory and industrial applications include transfer of fluids from one container into another. Varying the size of cylinder 30 would determine the capacity of the stroke volume of the pumping action.

Figure 7:
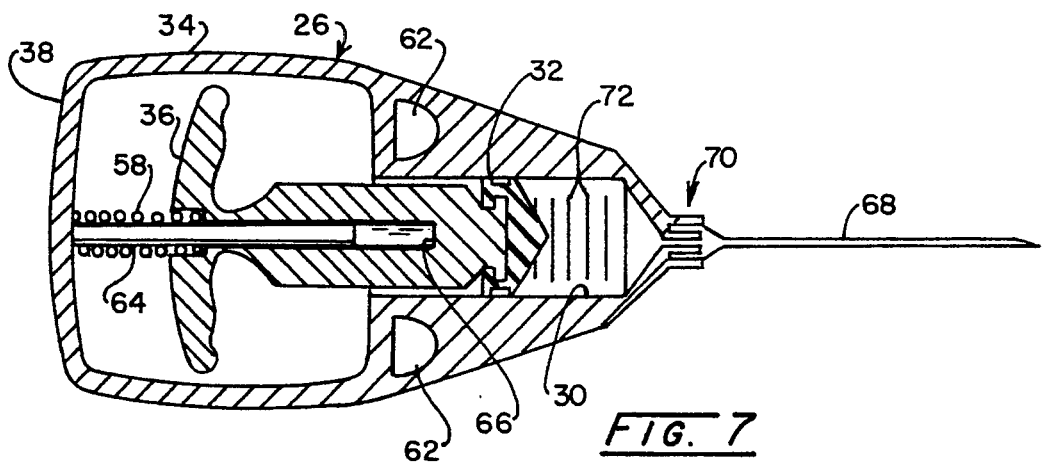
FIG. 7 is a sectional view of a sixth embodiment of the invention similar in function to the FIG. 6 embodiment.

FIG. 7 is an alternate embodiment of FIG. 6 wherein the valves are absent and indicia 72 are embossed on the exterior of cylinder 30 or otherwise incorporated such that a physician may observe the piston as he withdraws it by squeezing the handle 36 and the remote part 38 of the loop until he has withdrawn the desired amount of fluid into cylinder 30 following which biasing means 58 and 64 can effect the automatic injection of this fluid into a body or vessel. This embodiment has many medical applications including the automatic injection of medications, dyes, and contrast agents, as well as laboratory and industrial applications.

Figure 8:
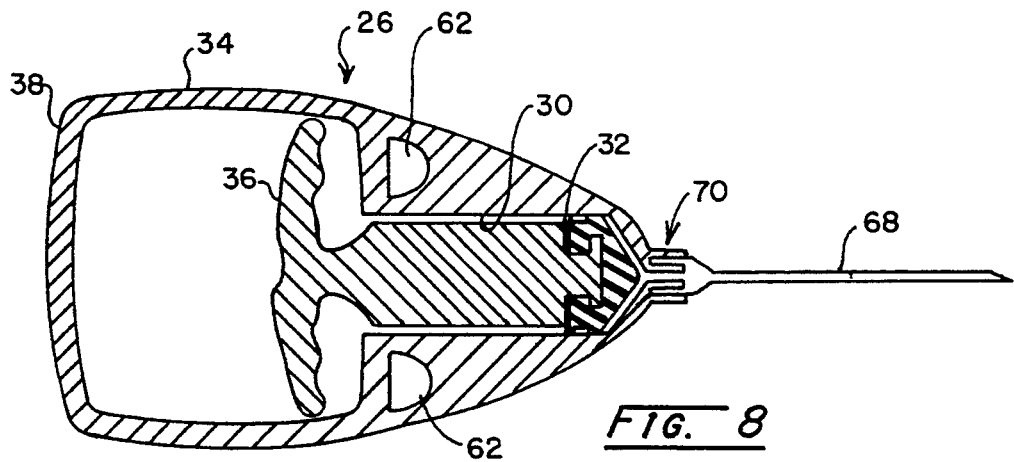
FIG. 8 is a sectional view of a seventh embodiment of the invention similar in function to the FIG. 6 embodiment.

FIG. 8 is a modification of the embodiments illustrated in FIGS. 6 and 7 in that the biasing means 58 and 64 are absent. The needle may be used to withdraw (aspirate) or inject fluids, or to perform biopsies of tissues such as liver, kidney, chorionic villus sampling, etc. wherein once the needle penetrates the tissue, vacuum is generated by pulling the handle 36 causing the tissue to enter the needle 68. Any currently available common needle or specialized biopsy needle may be fitted by luer lock at end 70 of frame 26. The sample obtained is contained in the cylinder 30 or retrieved from the needle lumen 68 in the fashion commonly done in the field.

Having thus described the invention in its preferred embodiment, it will be clear that modifications may be made without departing from the spirit of the invention. Also the language used to describe the inventive concept and the drawings accompanying the application to illustrate the same are not intended to be limiting on the invention. Rather it is intended that the invention be limited only by the scope of the appended claims.

We claim:

1. A manually operable medical device comprising,
    means forming a cylinder with an axis,
    a medical tool attached to said cylinder means, said medical tool comprises a cup for attachment to the head of a fetus,
    means forming a duct leading from said medical tool to one end of said cylinder means to provide fluid communication between said tool and said one end of said cylinder means by way of said duct means,
    a piston having an axis being mounted to reciprocate coaxially in said cylinder means and configured to reciprocate in said cylinder means in response to manually applied force to an end of said piston most remote from said one end of said cylinder means, said piston including a handle at said remote end, said handle extending transverse to said axes,
    a rigid closed loop connected to said cylinder means and circumscribing said handle, said loop including a surface for palm contact by an operator of said device upon said operator moving said piston to draw a vacuum in said cylinder means by engagement of said handle by the fingers of said operator.

2. The device of claim 1 including a first check valve in said duct means, said first check valve being configured to prevent fluid flow from said cylinder means to said tool,
    means forming an opening from said duct means, said opening means being located intermediate said first check valve and said cylinder means,
    a second check valve means located in said opening means and configured to allow fluid flow from said cylinder means.

3. The device of claim 2 including guide means secured to said loop for guiding the piston in its reciprocating movement.

4. The device of claim 3 including a spring engaging said loop for biasing said piston toward said one end of said cylinder means.

5. The device of claim 4 wherein said spring is a coil spring circumscribing said guide means.

6. The device of claim 5 wherein said guide means is a rod extending from said loop and coaxially aligned with a bore extending through said handle and into said piston, said bore being coaxially aligned with said piston.

7. The device of claim 6 including indicia on at least one of said cylinder means and said piston, said indicia being configured to show one of (1) the volume of the cylinder means between said one end of said cylinder means and the piston and (2) the degree of vacuum in said cylinder means.

8. The device of claim 3 wherein said guide means is a rod extending from said loop and coaxially aligned with a bore extending through said handle and into said piston, said bore being coaxially aligned with said piston.

9. The device of claim 1 including guide means secured to said loop for guiding the piston in its reciprocating movement.

10. The device of claim 7 including a spring engaging said loop for biasing said piston toward said one end of said cylinder means.

11. The device of claim 10 wherein said spring is a coil spring circumscribing said guide means.

12. The device of claim 10 wherein said guide means is a rod extending from said loop and coaxially aligned with a bore extending through said handle and into said piston, said bore being coaxially aligned with said piston.

13. The device of claim 1 including a spring engaging said loop for biasing said piston toward said one end of said cylinder means.

14. The device of claim 1 including a pair of finger sized openings in said cylinder means to accommodate two fingers of an operator upon a squeezing of said handle by the operator's hand to urge said piston toward said one end of said cylinder means.

15. The device of claim 14 including indicia on at least one of said cylinder means and said piston, said indicia being configured to show one of (1) the volume of the cylinder means between said one end of said cylinder means and the piston and (2) the degree of vacuum in said cylinder means.

16. The device of claim 1 including a valve to open the cylinder means to atmospheric pressure to relieve the vacuum without moving said piston.

17. The device of claim 16 including a first check valve in said duct means, said first check valve being configured to prevent fluid flow from said cylinder means to said tool,
    means forming an opening from said duct means, said opening means being located intermediate said first check valve and said cylinder means,
    a second check valve means located in said opening means and configured to allow fluid flow from said cylinder means.

18. The device of claim 17 including guide means secured to said loop for guiding the piston in its reciprocating movement.

19. The device of claim 18 including a spring engaging said loop for biasing said piston toward said one end of said cylinder means.

20. The device of claim 19 wherein said spring is a coil spring circumscribing said guide means.

21. The device of claim 20 wherein said guide means is a rod extending from said loop and coaxially aligned with a bore extending through said handle and into said piston, said bore being coaxially aligned with said piston.

22. The device of claim 16 including guide means secured to said loop for guiding the piston in its reciprocating movement.

23. The device of claim 22 including a spring engaging said loop for biasing said piston toward said one end of said cylinder means.

24. The device of claim 23 wherein said spring is a coil spring circumscribing said guide means.

25. The device of claim 24 wherein said guide means is a rod extending from said loop and coaxially aligned with a bore extending through said handle and into said piston, and bore being coaxially aligned with said piston.

26. A manually operable medical device comprising,
means forming a cylinder with an axis,
a medical tool attached to said cylinder means,
means forming a duct leading from said medical tool to one end of said cylinder means to provide fluid communication between said tool and said one end of said cylinder means by way of said duct means,
a piston having an axis being mounted to reciprocate coaxially in said cylinder means and configured to reciprocate in said cylinder means in response to manually applied force to an end of said piston most remote from said one end of said cylinder means, said piston including a handle at said remote end, said handle extending transverse to said axes,
a rigid closed loop connected to said cylinder means and circumscribing said handle, said loop including a surface for palm contact by an operator of said device upon said operator moving said piston to draw a vacuum in said cylinder means by engagement of said handle by the fingers of said operator,
a first check valve in said duct means, said first check valve being configured to prevent fluid flow from said cylinder means to said tool,
means forming an opening from said duct means, said opening means being located intermediate said first check valve and said cylinder means,
a second check valve means located in said opening means and configured to allow fluid flow from said cylinder means.

27. A manually operable medical device comprising,
means forming a cylinder with an axis,
a medical tool attached to said cylinder means,
means forming a duct leading from said medical tool to one end of said cylinder means to provide fluid communication between said tool and said one end of said cylinder means by way of said duct means,
a piston having an axis being mounted to reciprocate coaxially in said cylinder means and configured to reciprocate in said cylinder means in response to manually applied force to an end of said piston most remote from said one end of said cylinder means, said piston including a handle at said remote end, said handle extending transverse to said axes,
a rigid closed loop connected to said cylinder means and circumscribing said handle, said loop including a surface for palm contact by an operator of said device upon said operator moving said piston to draw a vacuum in said cylinder means by engagement of said handle by the fingers of said operator,
a spring engaging said loop for biasing said piston toward said one end of said cylinder means.

28. A manually operable medical device comprising,
means forming a cylinder with an axis,
a medical tool attached to said cylinder means,
means forming a duct leading from said medical tool to one end of said cylinder means to provide fluid communication between said tool and said one end of said cylinder means by way of said duct means,
a piston having an axis being mounted to reciprocate coaxially in said cylinder means and configured to reciprocate in said cylinder means in response to manually applied force to an end of said piston most remote from said one end of said cylinder means, said piston including a handle at said remote end, said handle extending transverse to said axes,
a rigid closed loop connected to said cylinder means and circumscribing said handle, said loop including a surface for palm contact by an operator of said device upon said operator moving said piston to draw a vacuum in said cylinder means by engagement of said handle by the fingers of said operator,
a valve to open the duct means to atmospheric pressure to relieve the vacuum without moving said piston.

* * * * *